United States Patent [19]
Maryan

[11] Patent Number: 5,250,051
[45] Date of Patent: Oct. 5, 1993

[54] ACETABULAR CUP POSITIONER WITH SLAPHAMMER MECHANISM FOR THE REMOVAL OF THE SIGHTING GUIDE

[75] Inventor: John P. Maryan, Anderson, Ind.

[73] Assignee: Zimmer, Inc., Warsaw, Ind.

[21] Appl. No.: 14,610

[22] Filed: Feb. 8, 1993

[51] Int. Cl.5 .............................................. A61B 17/00
[52] U.S. Cl. ........................................ 606/91; 606/53; 606/86; 606/100; 81/27
[58] Field of Search ................... 606/1, 53, 86, 81, 90, 606/91, 99, 100; 623/16, 22; 81/27; 433/146, 147

[56] References Cited

U.S. PATENT DOCUMENTS

| | | | |
|---|---|---|---|
| D. 284,889 | 7/1986 | Kenna | D24/26 |
| D. 331,461 | 12/1992 | Lester | D24/140 |
| 3,859,992 | 1/1975 | Amstutz | 606/91 |
| 4,222,382 | 9/1980 | Antonsson et al. | |
| 4,305,394 | 12/1981 | Bertuch, Jr. | |
| 4,475,549 | 10/1984 | Oh | |
| 4,632,111 | 12/1986 | Roche | |
| 4,677,972 | 7/1987 | Tornier | 606/91 |
| 4,716,894 | 1/1988 | Lazzeri et al. | |
| 4,993,410 | 2/1991 | Kimsey | 606/100 |
| 5,169,402 | 12/1992 | Elloy | 606/85 |
| 5,171,243 | 12/1992 | Kashuba et al. | 606/86 |
| 5,171,312 | 12/1992 | Salyer | 606/81 |

FOREIGN PATENT DOCUMENTS

WO86/05384 1/1986 PCT Int'l Appl. .

OTHER PUBLICATIONS

Advertisement—JBJS Jul., 1983 Issue 65-A.
JBJS, Oct. 1983 Issue 65-A, p. 1090.

*Primary Examiner*—Stephen C. Pellegrino
*Assistant Examiner*—Jeffrey A. Schmidt
*Attorney, Agent, or Firm*—Todd A. Dawson

[57] ABSTRACT

The acetabular cup positioner of this invention provides for a sighting guide which is removable connected to the shaft of the cup positioner by a tapered locking configuration. The taper lock provides for a secure connection of the sighting guide to the shaft of the cup positioner which enhances the accuracy of the device. The taper lock provides such a strong lock that in order to provide for its removal, the cup positioner of the invention includes a slaphammer carrier on the shaft of the guide which may be employed by the surgeon to remove the guide from the positioner without undue effort.

5 Claims, 3 Drawing Sheets

ACETABULAR CUP POSITIONER WITH SLAPHAMMER MECHANISM FOR THE REMOVAL OF THE SIGHTING GUIDE

FIELD OF THE INVENTION

This invention relates to acetabular cup positioners as used in the total hip arthroplasty and has specific relevance to a cup positioner with a slaphammer mechanism for the removal of the sighting guide.

BACKGROUND OF THE INVENTION

Acetabular cup positioners are used during total hip arthroplasty to assist the surgeon in positioning the prosthetic acetabular cup within the prepared acetabulum of the patient. Typically, the prosthetic cup will include a threaded central opening for accommodating a threaded stud of the cup positioner. An important process during positioning of the cup is to align the cup with the bodies anatomical axis to ensure proper function of the prosthetic joint. To assist the surgeon in aligning the cup, a wide multitude of sighting guides have been developed. Some of these sighting guides are removable to enable the positioner to be screwed off the acetabular cup once positioned.

SUMMARY OF THE INVENTION

The acetabular cup positioner of this invention provides for a sighting guide which is removable connected to the shaft of the cup positioner by a tapered locking configuration. The taper lock provides for a secure connection of the sighting guide to the shaft of the cup positioner which enhances the accuracy of the device. The taper lock provides such a strong lock that in order to provide for its removal, the cup positioner of the invention includes a slaphammer carried on the shaft of the guide which may be employed by the surgeon to remove the guide from the positioner without undue effort.

Accordingly, it is an object of the invention to provide for a novel prosthetic acetabular cup positioner.

Another object of the invention is to provide for a novel cup positioner having a removable sighting guide.

Another object of the invention is to provide for a novel cup positioner having a slaphammer mechanism carried on the sighting guide to provide for the removal of the sighting guide from the positioner shaft.

Other objects of the invention will become apparent upon a reading of the following description taken with the accompanying drawings.

DESCRIPTION OF THE PREFERRED EMBODIMENT

The preferred embodiment herein described is not intended to be exhaustive or to limit the invention to the precise form disclosed. Rather, it is chosen and described to best explain the invention so that others skilled in the art might utilize its teachings.

Figure 1:
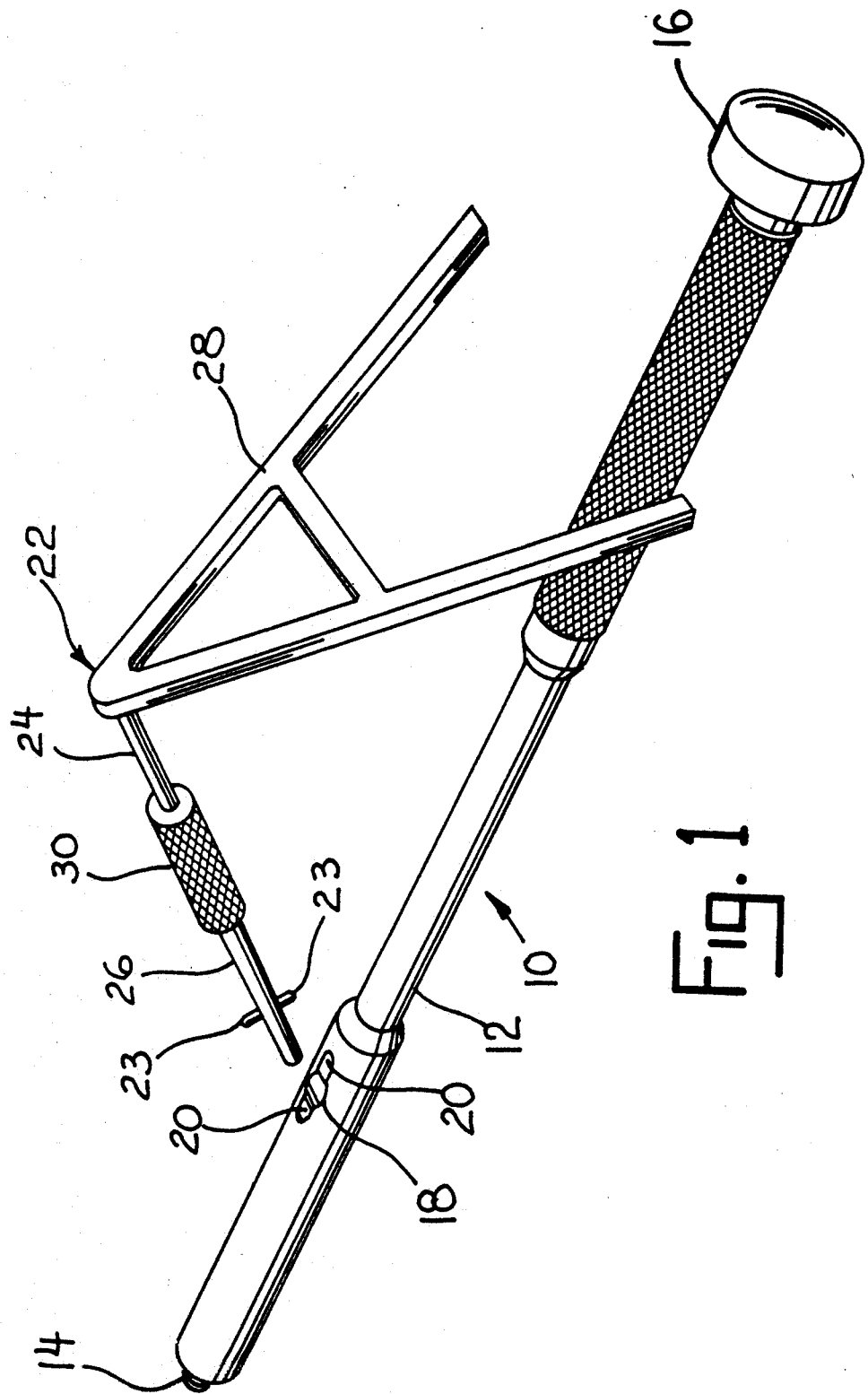
FIG. 1 is a perspective view of the acetabular cup positioner of the invention with the sighting guide disconnected from the positioned shaft.
Figure 2:
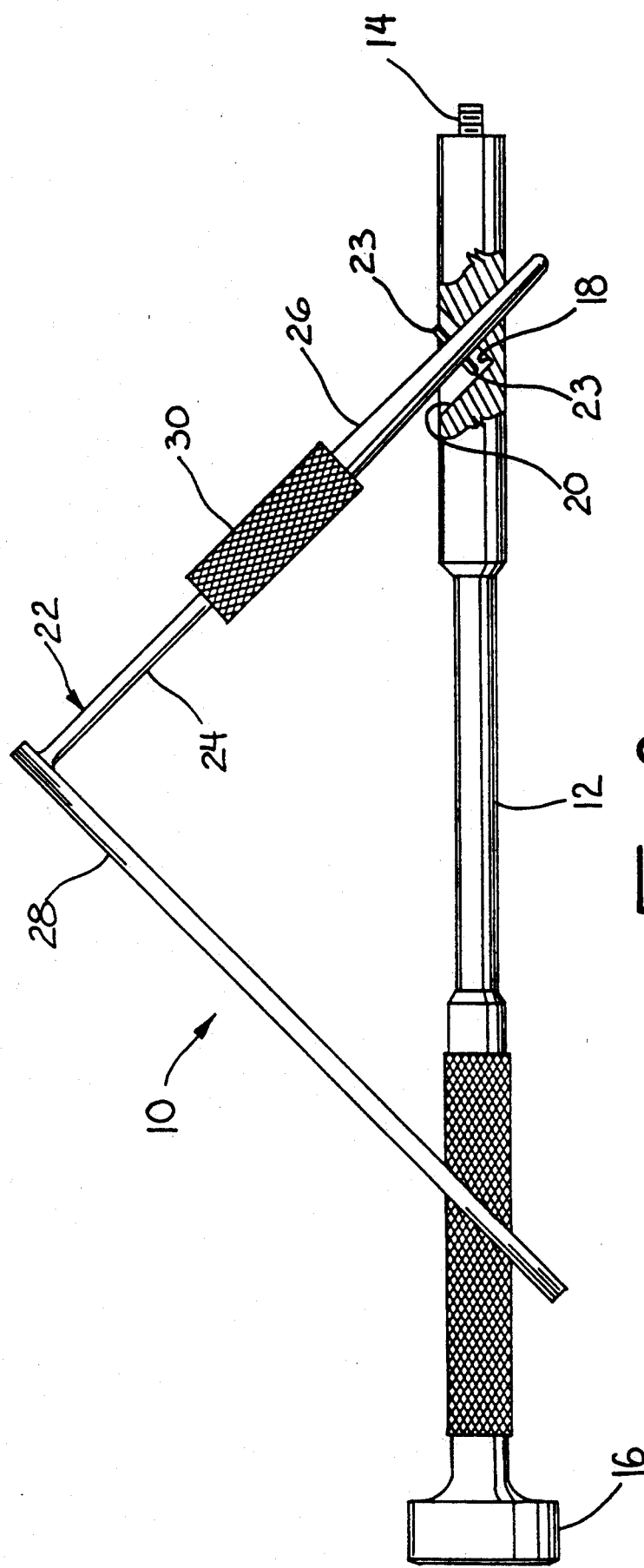
FIG. 2 is an elevational view of the invention with portions cut away for illustrative purposes.
Figure 3:
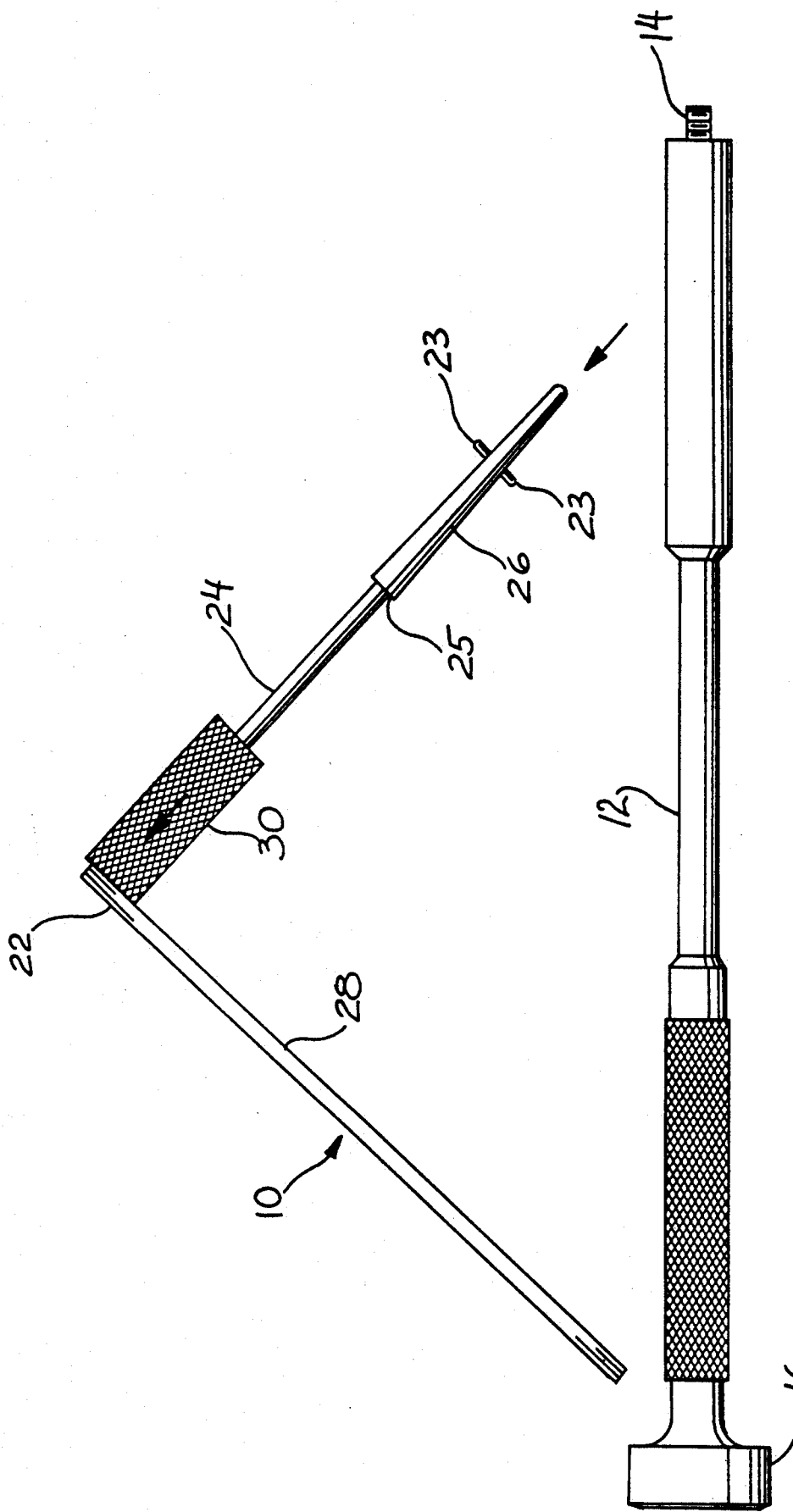
FIG. 3 is an elevational view of the invention with the sighting guide removed from the positioner shaft and the slaphammer mechanism in a striking position.

Referring now to the drawings, prosthetic acetabular cup positioner 10 (hereinafter positioner 10) includes a main shaft 12 having a threaded stud 14 extending longitudinally out one end and a head 16 connected to an opposite end. Threaded stud 14 is configured for turning within a threaded central bore of a prosthetic acetabular cup (not shown) as is well known in the industry. Head 16 provides an impact surface as is also well known in the art. A tapered through bore 18 is formed in shaft 12 at an angle as illustrated in FIG. 2. A pair of key ways 20 are formed in shaft 12 in communication with through bore 18.

Sighting guide 22 includes a generally cylindrical shaft 24 terminating in a tapered distal end 26. A shoulder 25 is formed at the junction of tapered distal end 26 and the generally cylindrical shaft of sighting guide 22. A pair of alignment pins 23 extend generally transversely from the tapered distal end of the sighting guide. The opposite end of guide 22 is connected to an A-shaped alignment guide 28. A-shaped alignment guide 28 provides a means for the surgeon to visually check the alignment of the acetabular cup with anatomical check points on the patient as is well know in the art. A cylindrical slaphammer mechanism 30 having a central bore is carried on the cylindrical shaft 24 of sighting guide 22 and is shiftable between a first position adjacent the shoulder 25 and a second position adjacent sighting guide 22. Slaphammer 30 is a generally solid cylinder of metal with the central bore formed therethrough.

In use, the surgeon rotates an acetabular cup onto the stud 14 of shaft 12 and inserts the tapered distal end 26 of sighting guide 22 into the tapered through bore 18 such that alignment pins 23 are accommodated within the key ways 20 formed adjacent the throughbore. The surgeon may gently tap the sighting guide to securely engage the tapered distal end 26 and tapered bore 18 in a tight fit. The tapered distal end and tapered bore configuration for mating two components is well known in the art and is generally referred to as a Morse Taper.

Once the surgeon has properly sighted and impacted the acetabular cup into the prepared acetabulum of the patient, the cup positioner needs to be rotated off of the cup. However, with sighting guide 22 attached such rotation is impossible. Therefore, to remove the sighting guide 22, the surgeon grasps the slaphammer mechanism 30 and briskly slides the slaphammer into repeated contact with the A-shaped guide 28 until the tapered distal end disengages from the tapered bore. Once the sighting guide is removed, the surgeon may easily rotate the main shaft 12 relative to the acetabular cup for removal therefrom.

It should be understood that the application is not to be limited to an A-shaped alignment guide as illustrated but has application to a wide variety of alignment guides.

Further, it should be understood that the invention is not to be limited by the precise form disclosed but may be modified within the keeping of the appended claims.

I claim:

1. A sighting guide for an acetabular cup positioner, said sighting guide including a connection means configured for frictionally connecting the sighting guide to the cup positioner, sighting means connected to said connection means for providing alignment indication and disengaging means carried by said sighting guide for disengaging the connection means to remove the sighting guide from the cup positioner, said disengaging means being abruptly shiftable from a first position adjacent said connection means to a second position adjacent said sighting means.

2. The sighting guide of claim 1 wherein said connection means includes a tapered shaft.

3. The sighting guide of claim 2 wherein including a generally cylindrical shaft extending between the tapered shaft and the sighting means, said disengaging means being a cylinder having a central bore for accommodating said cylindrical shaft and being shiftable between said first and second position.

4. A positioner configured for connection to a prosthetic acetabular cup, said positioner including a main shaft having a means for connecting the positioner to a prosthetic acetabular cup, a sighting means connected to said main shaft and being configured to provide visual alignment guides to a user for positioning the acetabular cup, the sighting means including a shaft for connection to the main shaft and an alignment indicator connected to the shaft of the sighting means, the positioner further including slaphammer means carried by the shaft of said sighting means for disengaging the sighting means from said main shaft, said slaphammer means being shiftable between a first position spaced from said alignment indicator and a second position in contact with said alignment indicator such that as said slaphammer means is shifted abruptly from said first position into said second position, the shaft of the sighting means is disengaged from the main shaft.

5. A positioner configured for connection to a prosthetic acetabular cup, said positioner including a main shaft having a means for connecting the positioner to a prosthetic acetabular cup, a sighting guide connected to said main shaft and being configured to provide visual alignment to a user for positioning the acetabular cup within a prepared acetabulum of a patient, the sighting guide including a shaft having a cylindrical portion and a tapered distal end for frictional accommodation within a tapered bore formed in the main shaft, the sighting guide further including alignment guides extending from said cylindrical shaft, the positioner further including a slaphammer slidably carried by the shaft of said sighting means shiftable between a first position spaced from said alignment guides and a second position in contact with said alignment guides such that as said slaphammer is shifted abruptly from said first position into said second position, the tapered distal end of the sighting guide is pulled from the tapered bore.

* * * * *